United States Patent
Bartels et al.

(12) 
(10) Patent No.: US 6,485,528 B1
(45) Date of Patent: Nov. 26, 2002

(54) AGENTS FOR TREATING KERATIN FIBERS

(75) Inventors: Holger Bartels, Hamburg (DE);
Wolfgang Wolff, Bargteheide (DE);
Stefan Hoepfner, Hamburg (DE);
Sandra Rohweder, Hamburg (DE)

(73) Assignee: Hans Schwarzkopf GmbH & Co. KG, Hamburg (DE)

( * ) Notice: Subject to any disclaimer, the term of this patent is extended or adjusted under 35 U.S.C. 154(b) by 0 days.

(21) Appl. No.: 09/581,035

(22) PCT Filed: Dec. 4, 1998

(86) PCT No.: PCT/EP98/07905

§ 371 (c)(1),
(2), (4) Date: Oct. 10, 2000

(87) PCT Pub. No.: WO99/30673

PCT Pub. Date: Jun. 24, 1999

(30) Foreign Application Priority Data

Dec. 13, 1997 (DE) .......................................... 197 55 420

(51) Int. Cl.$^7$ .................................................. A61K 7/13
(52) U.S. Cl. ....................... 8/405; 8/405; 8/406; 8/409; 8/410; 8/411
(58) Field of Search ........................... 8/405, 406, 409, 8/410, 411

(56) References Cited

U.S. PATENT DOCUMENTS 5,961,664 A * 10/1999 Anderson et al. .............. 8/405

FOREIGN PATENT DOCUMENTS

| EP | 0 493 392 | 3/1996 |
|---|---|---|
| FR | 2 718 352 | 10/1995 |
| WO | WO91/01127 | 2/1991 |

OTHER PUBLICATIONS

EU Inventory of Cosmetic Ingredients, Colipa, Mar. 1996—on diskette.
K. H. Bauer et al., Pharmazeutische Technologie, Gustav Fischer Verlag, Stuttgart, Jena, Lubeck Ulm, $4^{th}$ Edition, pp. 315–323, 1997.
K. H. Bauer et al., Pharmazeutische Technologie, Gustav Fischer Verlag, Stuttgart, Jena, Lubeck Ulm, $4^{th}$ Edition, pp. 324–335, 1997.
J. Korn, Die Neue Verpackung, 10, pp. 1150–1155, 1962.
The Science of Hair Care, Chapter 7, pp. 235–261, published as vol. 7 of Dermatology, Marcel Dekker, Inc., NY/Basle (1986).
The Science of Hair Care, Chapter 8, pp. 263–268 published as vol. 7 of Dermatology, Marcel Dekker, Inc., NY/Basle (1986).
K. Schrader, Grundlagen un Rezepturen der Kosmetika [Bases and Formulations in Cosmetics], $2^{nd}$ Edition, pp. 782–799, Huethig Buch Verlag, Heidelberg, Germany, 1989.

* cited by examiner

Primary Examiner—Yogendra N. Gupta
Assistant Examiner—Eisa Elhilo
(74) Attorney, Agent, or Firm—Stephen D. Harper; Glenn E. J. Murphy

(57) ABSTRACT

An agent for treating keratin fibers, comprising an aqueous preparation A and a preparation B that comprises a constituent that is not storage-stable in the presence of preparation A, the constituent in B being chosen from the group consisting of perfume oils and vitamins, provitamins, and derivatives thereof, the preparation B being contained in and spatially separated from the aqueous preparation A by an envelope of material that permits preparations A and B to mix at 38° C. within 5 minutes after the envelope containing preparation B is added to preparation A.

9 Claims, No Drawings

AGENTS FOR TREATING KERATIN FIBERS

BACKGROUND OF THE INVENTION

Description of the Invention

The invention relates to agents for treating keratin fibers, consisting of at least two spatially separate preparations, to the use thereof, and to a method of treating human hair.

The requirements which users of agents for treating keratin fibers, in particular hair treatment agents, place on these agents have continuously increased over time. This has led inter alia to these agents consisting in many cases of an ever greater number of components in order to achieve all of the effects desired by the user in the most optimal manner possible. However, as the complexity of these mixtures increases, so too does the number of active ingredient combinations which, despite having the desired properties in a single formulation, particularly in the case of an aqueous mixture, are no longer storage-stable.

In the field of hair treatment, a number of agents are known which are in the form of separate preparations which are either mixed directly prior to application to the hair, or are applied to the hair one after the other in separate steps; for ease of handling for the user and not least to minimize packaging expenditure, in the development of new products, wherever possible formulation in the form of one agent is desired.

Should formulation in separate preparations which have to be mixed prior to application to the hair be absolutely unavoidable, then the mixing operation should be as rapid and uncomplicated as possible, and, as already mentioned above, the additional packaging expenditure be kept as low as possible.

We have now found that these requirements are satisfied to a high degree when the component to be stored separately, or the components to be stored separately are provided with an envelope which, when the 5 preparations are combined, permits mixing of the components of the two preparations in a period of time which is tolerable for the user. The period of time accepted by the user can generally be regarded as an interval of up to 5 minutes if the mixing operation of the two preparations is not combined with any further, laborious procedures, e.g. continuous stirring, of any kind.

The invention must then firstly provide an agent for treating keratin fibers, consisting of at least one aqueous preparation A and, spatially separate therefrom, at least one preparation B, which has an envelope of preparation B made from a material which permits the components of the two preparations to mix at 38° C. within 5 minutes when the preparation B is added to a preparation A.

A number of hair treatment agents are applied to the hair in gently warmed form. Warming is generally achieved by combining components which liberate heat on mixing. One component is often an anhydrous salt which dissolves in an aqueous phase with the liberation of heat; alternatively, it is also possible to use heats of neutralization, heats of mixing liquid components etc. The quantitative ratios of the components to be mixed are in these cases preferably adjusted such that the mixture adopts a temperature slightly above the temperature of the human body, i.e. about 38° C., within a very short time, i.e. a few seconds. In the case of this type of agent, it is therefore sufficient for the components of the enveloped preparation B to be mixed with the components of the aqueous preparation A within 5 minutes at a temperature of 38° C. Apart from occasional shaking of the mixture, no further activities on the part of the user should be necessary here.

The overwhelming majority of hair treatment agents are stored at room temperature and also applied to the hair at this temperature. According to a preferred embodiment of the invention, the envelope of the preparation B is thus chosen such that mixing of the components of the preparations A and B takes place within a maximum of 5 minutes even at room temperature, i.e. in particular a temperature of 20° C.

According to a preferred embodiment of the invention, the envelope of component B is a capsule.

Corresponding envelopes in capsule form are known from the field of pharmacy. One type of these capsules are films in capsule form, in which the substances to be enveloped are completely enclosed by a layer of the enveloping material, and the enveloped substances can be released again only following destruction of the envelope. In this connection, suitable materials for the envelope are preferably certain cellulose derivatives, polyacrylates, polymethacrylates, polyvinylpyrrolidones, and, in particular, polyvinyl alcohols. In this connection, express reference is made to the monograph by K. H. Bauer, K. H. Frömming and C. Führer, Pharmazeutische Technologie [Pharmaceutical Technology], Gustav Fischer Verlag, Stuttgart, Jena, Lübeck, Ulm, 4th edition, 1997, pages 315–323.

Two-part capsules generally consist of two cylindrical halves, each sealed at one end. The internal diameter of one half, which is also referred to as the capsule cap, is slightly larger than the external diameter of the other half, referred to as the capsule base, meaning that the two halves can be inserted into one another to envelope the component to be enclosed, the capsule being "bolted" by special devices. This type of capsule is also referred to as hard capsules and is a preferred envelope according to the invention. Suitable capsule materials are in principle both gelatins and also synthetic or natural polymers. Polyvinyl alcohol has proven to be a particularly suitable envelope material.

In accordance with a first preferred embodiment, the entire hard capsule consists of polyvinyl alcohol.

It may, however, also be provided that only part of the hard capsule, in particular the capsule cap or parts of the capsule cap, consists of a water-soluble material in accordance with the definition according to the invention. It is then possible, for example, to prepare the capsule base from a less water-soluble material. This allows greater flexibility in setting the desired mechanical properties, e.g. the rigidity, of the capsule. With regard to this envelope form, reference is likewise made to the monograph mentioned above by K. H. Bauer, K.-H. Frömming and C. Führer, pages 324–335.

The envelope can, however, also take the form of a pouch. Such pouches are produced in a known manner from polymer films, from which the individual pouches containing the ingredients are produced by sealing or gluing. Further information about such pouches is given, for example, in the article by J. Korn, Die Neue Verpackung [The New Package], 10, 1150–1155 (1962), and EP 493 392, in which pouches made of polyvinyl alcohol are disclosed for the dust-free packaging of bleaches.

Because of better handleability, particularly when the preparation B is added to a preparation A in a bottle with a relatively narrow neck, an envelope in the form of a capsule is preferred according to the invention.

It is further preferred that the envelope material consists of substances which additionally develop positive properties in hair treatment agents. In this connection as well, polyvinyl alcohol is a preferred envelope material because of its conditioning properties.

The thickness of the envelope is chosen by the person skilled in the art such that, on the one hand, a hermetic seal of the preparations to be enveloped is ensured, but, on the other hand, the mixing of the preparations A and B is not unnecessarily prolonged by too thick an envelope. Envelope thicknesses in the range from 10 to 30 micrometers have proven particularly suitable within the scope of the teaching according to the invention.

The teaching according to the invention is particularly suitable for agents which, in the preparation B, contain a constituent which is not storage-stable in the preparation A.

In accordance with a first preferred embodiment, this constituent is a perfume oil, a particular perfume component or a mixture of perfume oils.

Certain hair treatment agents comprise active ingredients which are unavoidable for achieving the desired properties or for formulating the agent, but develop such an intrinsic odor that perfume is virtually essential in order to achieve acceptance on the part of the user. Examples thereof are, in particular, permanent wave agents with a content of organosulfo compounds such as thioglycolic acid, salts and/or derivatives thereof as reducing agent, and of ammonia or lower amines for setting the pH. Both because of the reducing agents present in the agent and also because of said alkylating agents, the person skilled in the art is very limited with regard to perfume components which can be used if his task is to formulate agents which are storage-stable for months. On the other hand, most of the perfume components which are unsuitable for such storage-stable agents are sufficiently stable in the agents for a short period of time of up to an hour, i.e. for the period of time of actual use, to develop the desired scent effect.

Other agents according to this embodiment are permanent wave fixatives which are usually very acidic and contain up to 12% by weight of an oxidizing agent, in particular hydrogen peroxide. Under these conditions too, although many perfume components are stable for the period of time of application to the hair, they are not stable for months or years. Other agents in which incompatibilities arise between perfume components and further constituents are, for example, oxidation colorants and bleaching agents.

The teaching according to the invention is particularly suitable for perfume oils and perfume components which have an aldehyde function and/or a C—C-double bond which optionally stands in conjugation to the aldehyde function. Other perfume components which have a primary alcohol function or an ester function are likewise preferred compounds within the scope of this embodiment of the invention.

Furthermore, perfume components of the "fruity" scent direction in very many cases have unsatisfactory stabilities in agents which have strong reducing or oxidizing agents. The teaching according to the invention has proven extraordinarily well suited for these perfume components as well. Finally, the same is also true for so-called sandalwood fragrances, both of natural and, in particular, of synthetic provenance.

According to a second preferred embodiment, the incompatible constituent is a substance from the group formed from vitamins, provitamins and their derivatives. This group comprises, for example, panthenol and its derivatives, such as pantothenic acid, pantothenyl esters and ethers and pantothenyl ethyl ether. Panthenol in particular is itself not sufficiently storage-stable in strongly alkaline or acidic, aqueous media, and in preparations containing oxidizing agents. Other vitamins from the B complex are the vitamins $B_2$, $B_6$, $B_{12}$ and nicotinamide. Retinol and other substances which are referred to as vitamin A are, for example, sensitive toward oxidizing agents, and the same is true for vitamin E.

The nature of the hair treatment agent is not subject in principle to any limitations. It can, for example, be a cleansing agent, such as shampoos, care agents, such as hair treatments and hair rinses, setting agents, such as hair setting lotions, hair sprays and blow-waving lotions, permanent shaping agents, such as permanent waving agents and fixatives, coloring agents, such as bleaching agents, oxidation dyes and tinting agents based on direct dyes, hair tonics and split-end fluids. Accordingly, the preparations can be formulated as aqueous or aqueous-alcoholic (with a maximum of 15% by weight of alkanol, based on the total agent) solutions, emulsions, gels, creams, aerosols or lotions.

The agents according to the invention can further comprise all active ingredients, additives and auxiliaries known in such preparations. In many cases, the agents comprise at least one surfactant, where, in principle, both anionic and also zwitterionic, ampholytic, nonionic and cationic surfactants are suitable. In many cases, however, it has proven advantageous to choose the surfactants from anionic, zwitterionic or nonionic surfactants. Anionic surfactants may be very particularly preferred in this connection.

Examples of surfactants which can be used according to the invention are:

anionic surfactants, such as, in particular, soaps of fatty acids, alkyl sulfates, alkylpolyglycol ether sulfates and ether carboxylic acids having 10 to 18 carbon atoms in the alkyl group and up to 12 glycol ether groups in the molecule, and a sulfosuccinic mono- and dialkyl ester having 8 to 18 carbon atoms in the alkyl group and sulfosuccinic monoalkyl polyoxyethyl ester having 8 to 18 carbon atoms in the alkyl group and 1 to 6 oxyethyl groups, nonionogenic surfactants such as, in particular, addition products of from 2 to 30 mol of ethylene oxide and/or 0 to 5 mol of propylene oxide to linear fatty alcohols having 8 to 22 carbon atoms, to fatty acids having 12 to 22 carbon atoms and to alkyl phenols having 8 to 15 carbon atoms in the alkyl group, $C_{12}$–$C_{22}$-fatty acid mono- and diesters of addition products of from 1 to 30 mol of ethylene oxide to glycerol, $C_8$–$C_{22}$-alkyl mono- and oligoglycosides and the ethoxylated analogs thereof, and addition products of from 5 to 60 mol of ethylene oxide to castor oil and hydrogenated castor oil, zwitterionic surfactants, in particular so-called betaines as the N-alkyl-N,N-dimethylammonium glycinates, for example cocoalkyldimethylammonium glycinate, N-acylaminopropyl-N,N-dimethylammonium glycinates, for example cocoacylaminopropyl-dimethylammonioum glycinate, and 2-alkyl-3-carboxymethyl-3-hydroxyethylimidazoline having in each case 8 to 18 carbon atoms in the alkyl or acyl group, and cocoacylaminoethylhydroxy-ethylcarboxymethyl glycinate, ampholytic surfactants, such as N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group, cationic surfactants of the quaternary ammonium compound type, e.g. ammonium halides, in particular chlorides and bromides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, behenyltrimethylammonium methosulfate, and the imidazolium compounds known under the INCI names Quaternium-27 and Quaternium-83. Other cationic surfactants which can be used are alkylamidoamines, such as the stearamidopropyldimethylamine commercially available under the name Tegoamid® S 18, and so-called ester quats, such as the N,N-bis(2-palmitoyloxyethyl)dimethylammonium chloride available commercially under the name Armocare® VGH-70, and the products sold under the tradename Dehyquart Examples of other active ingredients, auxiliaries and additives are nonionic polymers such as, for example, vinylpyrrolidone/vinyl acrylate copolymers, polyvinylpyrrolidone and vinylpyrrolidone/vinyl acetate copolymers and polysiloxanes, cationic polymers such as quaternized cellulose ethers, polysiloxanes containing quaternary groups, dimethyldiallylammonium chloride polymers, acrylamide/dimethyldiallylammonium chloride copolymers, dimethylaminoethylmethacrylate/-vinylpyrrolidone copolymers quaternized with diethyl sulfate, vinylpyrrolidone/imidazolinium methochloride copolymers and quaternized polyvinyl alcohol, zwitterionic and amphoteric polymers such as, for example, acrylamidopropyltrimethylammonium chloride/acrylate copolymers and octylacrylamide/methyl methacrylate/tert-butylaminoethyl methacrylate/2-hydroxypropyl methacrylate copolymers, anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butylacrylamide terpolymers, thickeners, such as agar agar, guar gum, alginates, xanthan gum, gum arabic, karaya gum, carob seed grain, linseed gums, dextrans, cellulose derivatives, e.g. methylcellulose, hydroxyalkylcellulose and carboxymethylcellulose, starch fractions and derivatives, such as amylose, amylopectin and dextrins, clays, such as, for example, bentonite or completely synthetic hydrocolloids, such as, for example, polyvinyl alcohol, structurants, such as glucose, maleic acid and lactic acid, hair-conditioning compounds, such as phospholipids, for example soya lecithin, egg-yolk lecithin and cephalins, and silicone oils, protein hydrolysates, in particular elastin, collagen, keratin, milk protein, soya protein, almond protein and wheat protein hydrolysates, the condensation products thereof with fatty acids, and quaternized protein hydrolysates, plant and honey extracts, such as, in particular, extracts from oak bark, stinging nettles, hamamelis, hops, camomile, burdock, horsetail, linden flowers, almond, aloe vera, coconut, mango, apricot, lemon, wheat, kiwi, melon, orange, grapefruit, sage, rosemary, birch, lady's-smock, wild thyme, yarrow, rest-harrow, meristem, ginseng and root ginger, dimethyl isosorbide and cyclodextrins, solubilizers, such as ethanol, isopropanol, ethylene glycol, propylene glycol, glycerol and diethylene glycol, antidandruff active ingredients, such as piroctone olamine and zinc omadine, alkalinizing agents, such as, for example, ammonia, monoethanolamine, 2-amino-2-methylpropanol and 2-amino-2-methyl-1,3-propanediol, other substances for adjusting the pH, active ingredients, such as allantoin, biotin, bisabolol, cholesterol, and pyrrolidonecarboxylic acids and salts thereof, light protection agents, bodying agents, such as sugar esters, polyol esters or polyol alkyl ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration substances, such as glycerol, propylene glycol monoethyl ether, carbonates, hydrogen carbonates, guanidines, ureas, and primary, secondary and tertiary phosphates, opacifiers, such as latex, styrene/PVP and styrene/acrylamide copolymers, pearlizing agents, such as ethylene glycol mono-and distearate, and PEG-3 distearate, complexing agents, such as EDTA, NTA, β-alaninediacetic acid and phosphonic acids, reducing agents, such as, for example, thioglycolic acid and derivatives thereof, thiolactic acid, cysteamine, thiomalic acid and α-mercaptoethanesulfonic acid, oxidizing agents, such as hydrogen peroxide, potassium bromate and sodium bromate and antioxidants.

With regard to the dyes which can be used in the hair colorants and tints according to the invention, reference is also expressly made to the monograph Ch. Zviak, The Science of Hair Care, Chapter 7 (pages 248–250; direct dyes), and Chapter 8, pages 264–267; oxidation dye precursors), published as Volume 7 of the series "Dermatology" (Ed.: Ch., Culnan and H. Maibach), Verlag Marcel Dekker Inc., New York, Basle, 1986, and the "European Inventory of Cosmetic Raw Materials", published by the European Union, obtainable in diskette form from the Bundesverband Deutscher Industrie-und Handelsunternehmen für Arneimittel, Reformwaren und Körperpflegemittel e.v. [Federal Association of German Industrial and Commercial Enterprises for Medicaments, Health Goods and Bodycare Products], Mannheim.

The pH of the agents according to the invention during use can in principle be between 2 and 11, the person skilled in the art being familiar with the preferred pH ranges for the various agents. To adjust the pH, virtually any acid which can be used for cosmetic purposes can be used. Usually, food acids are used. The term food acids means acids which are taken in in the course of usual food absorption and have positive effects on the human organism. Food acids are, for example, acetic acid, lactic acid, tartaric acid, citric acid, malic acid, ascorbic acid and gluconic acid. Within the scope of the invention, the use of citric acid and lactic acid is particularly preferred.

With regard to further constituents and quantitative ranges for the individual ingredients, reference is made to the handbooks known to the person skilled in the art, e.g. K. Schrader, Grundlagen und Rezepturen der Kosmetika [Bases and Formulations in Cosmetics], 2nd edition, Hüthig Buch Verlag, Heidelberg, 1989.

The teaching according to the invention of course also includes agents which contain a plurality of spatially separate preparations A, of which, however, at least one is an aqueous preparation. Likewise, the agent according to the invention can, if desired, also comprise a plurality of spatially separate preparations B, each of which is enveloped according to the teaching of the invention.

According to a specific embodiment of the teaching according to the invention, it may be desired to design the envelope of the preparation B such that mixing of the preparation B with an aqueous medium, such as the preparation A takes place only after a period of latency of 20 seconds, in particular 30 seconds. Thus, for example when a user with damp or wet hands puts a capsule containing the preparation B into a vessel (e.g. a bottle) containing the preparation A, the release of some of the preparation on to the hands during this operation is prevented. This may, particularly with regard to long-lasting perfume components, be an essential prerequisite for the practicability of the process and the acceptance by the user.

The invention further provides for the use of an agent as claimed in any of claims 1 to 10 for the treatment of human hair.

Finally, a third subject matter of the invention is a method of treating human hair, in which the preparations A and B of an agent as claimed in any of claims 1 to 10 are combined, and, following complete mixing of the ingredients, the resulting agent, is applied to the hair and optionally after a contact time of from 10 seconds to 45 minutes is rinsed off again.

What is claimed is:

1. An agent for treating keratin fibers, comprising an aqueous preparation A and a preparation B that comprises a constituent that is not storage-stable in the presence of preparation A, the constituent in B comprising one or more perfume oils, vitamins, provitamnins, or derivatives of vitamins or provitamins, the preparation B being contained in and spatially separated from the aqueous preparation A by an envelope of material that permits preparations A and B to mix at 38' C. within 5 minutes after the envelope containing preparation B is added to preparation A, and wherein the preparation B is free from incompatible agents selected from the group consisting of oxidation colorants, bleaching agents, pathenol, pathenol derivatives or mixture thereof.

2. The agent of claim 1, wherein the envelope of material permits preparations A and B to mix at 20° C. within 5 minutes after the envelope containing preparation B is added to preparation A.

3. The agent of claim 1, wherein the envelope of material is in the form of a capsule or pouch.

4. The agent of claim 3, wherein the wall thickness of the envelope is 10 to 30 micrometers.

5. The agent of claim 3, wherein the envelope comprises a uniform material.

6. The agent of claim 1, wherein the envelope material at least in part comprises polyvinyl alcohol.

7. The agent of claim 1, comprising a composition for oloring bleaching, or permanent shaping of hair.

8. A method of treating human hair, comprising the steps of (a) combining and mixing an aqueous preparation A and an envelope containing a preparation B that comprises a constituent that is not storage-stable in the presence of preparation A, the constituent in B comprising one or more perfume oils, vitamins, provitamins, or derivatives of vitamins or provitamins, where the envelope containing the preparation B comprises a material that permits the preparation A and B to mix at 38° C. within 5 minutes after the envelope containing preparation B is added to preparation A, wherein the preparation B is free from incompatible agents selected from the group consisting of oxidation colorants, bleaching agents, pathenol, pathenol derivatives or mixture thereof (b) applying the mixture to the hair; and (c) optionally musing the mixture from the hair after a contact time of 10 seconds to 45 minutes.

9. An agent for treating keratin fibers, comprising an aqueous preparation A and a preparation B that comprises a constituent that is not storage-stable in the presence of preparation A, the constituent in B comprising one or more perfume oils, vitamins, provitamins, or derivatives of vitamins or provitamins, the preparation B being contained in and spatially separated from the aqueous preparation A by an envelope of material that permits the preparations A and B to mix at 38° C. within 5 minutes after the envelope containing the preparation B is added to the preparation A, wherein the preparation B is free from incompatible agents selected from the group consisting of oxidation colorants, bleaching agents, pathenol, pathenol derivatives or mixture thereof and wherein the envelope has a wall thickness of from 10 micrometers to 30 micrometers.

* * * * *

UNITED STATES PATENT AND TRADEMARK OFFICE
CERTIFICATE OF CORRECTION

PATENT NO. : 6,485,528 B1
DATED : November 26, 2002
INVENTOR(S) : Holger Bartels et al.

It is certified that error appears in the above-identified patent and that said Letters Patent is hereby corrected as shown below:

<u>Column 7,</u>
Line 47, delete "provitamnins", and insert therefor -- provitamins --.
Line 51, delete "38' C.", and insert therefor -- 38º C. --.

<u>Column 8,</u>
Line 18, delete "oloring", and insert therefor -- coloring, --.
Line 32, after "thereof", insert -- ; --.
Line 33, delete "musing", and insert therefor -- rinsing --.

Signed and Sealed this

Ninth Day of September, 2003

JAMES E. ROGAN
*Director of the United States Patent and Trademark Office*